US011642008B2

(12) United States Patent
Shin et al.

(10) Patent No.: US 11,642,008 B2
(45) Date of Patent: May 9, 2023

(54) DETACHABLE ENDOSCOPE

(71) Applicant: TAEWOONG MEDICAL CO., LTD., Gimpo-si (KR)

(72) Inventors: Kyong Min Shin, Gyeonggi-do (KR); Sung Hwan Park, Gimpo-si (KR); Hyun Soo Ji, Gimpo-si (KR)

(73) Assignee: TAEWOONG MEDICAL CO., LTD., Gimpo-si (KR)

( * ) Notice: Subject to any disclaimer, the term of this patent is extended or adjusted under 35 U.S.C. 154(b) by 309 days.

(21) Appl. No.: 17/014,287

(22) Filed: Sep. 8, 2020

(65) Prior Publication Data

US 2021/0068621 A1 Mar. 11, 2021

(30) Foreign Application Priority Data

Sep. 11, 2019 (KR) .................. 10-2019-0112950

(51) Int. Cl.
*A61B 1/00* (2006.01)
*A61B 1/005* (2006.01)
*A61B 1/06* (2006.01)

(52) U.S. Cl.
CPC ...... *A61B 1/00105* (2013.01); *A61B 1/00009* (2013.01); *A61B 1/0057* (2013.01); *A61B 1/00073* (2013.01); *A61B 1/0661* (2013.01)

(58) Field of Classification Search
CPC .............. A61B 1/0057; A61B 1/00073; A61B 1/00124; A61B 1/00105; A61B 1/313
See application file for complete search history.

(56) References Cited

U.S. PATENT DOCUMENTS

| 4,203,430 A | * | 5/1980 | Takahashi | A61B 1/0052 600/149 |
| 5,359,994 A | * | 11/1994 | Krauter | A61B 1/0052 604/95.04 |
| 2005/0075538 A1 | * | 4/2005 | Banik | A61B 1/00096 600/152 |
| 2008/0125628 A1 | * | 5/2008 | Ueno | A61B 1/0052 600/130 |

FOREIGN PATENT DOCUMENTS

| KR | 10-0673412 B1 | 1/2007 |
| KR | 10-1091999 B1 | 12/2011 |
| KR | 10-1783225 B1 | 9/2017 |

* cited by examiner

*Primary Examiner* — John P Leubecker
*Assistant Examiner* — Jae Woo
(74) *Attorney, Agent, or Firm* — Bridgeway IP Law Group, PLLC; Jihun Kim (57) ABSTRACT

A detachable endoscope includes an insertion unit including an illuminating and image pickup unit, an operation unit configured to bendingly operate a front end of the insertion unit, and a detachable unit configured to detachably couple the insertion unit and the operation unit to each other, wherein the detachable unit includes: a first detachable module disposed at the insertion unit; and a second detachable module disposed at the operation unit, wherein the first detachable module includes: a first module main body disposed within a rear end of the insertion unit and having first, second, third and fourth rectilinear guide through-bores penetratingly formed longitudinally therein, and a central opening penetratingly formed at a center of the main body in a thickness direction of the main body.

7 Claims, 10 Drawing Sheets

DETACHABLE ENDOSCOPE

BACKGROUND OF THE INVENTION

1. Field of the Invention

The present invention relates to an endoscope. More specifically, the present invention relates to a detachable endoscope which can simply couple an insertion unit inserted into a body cavity to an operation unit that bendingly operates a front end of the insertion unit with each other for use in endoscopic surgery, and simply decouple the operation unit and the insertion unit from each other for storage or disinfect them for re-use after endoscopic surgery.

2. Description of Related Art

In general, surgery employing an endoscope, i.e., endoscopic surgery is performed such that a surgeon inserts a camera-equipped endoscope and a surgical instrument into a small body cavity without a making large incision, and then examines a patient's affected area through an image picked up by the endoscope inside the body.

In particular, endoscopic surgery originated from laparoscopic surgery has an advantage in that since a scarred part is relatively small owing to a small incised part and the amount of bleeding is less as compared to laparotomy, the recovery time of the patient is fast after endoscopic surgery.

In recent years, medical technologies have been developed enough to enable endoscopic surgery in almost all surgeries needing laparotomy as well as the case increases in which endoscopic surgery is applied in other medical fields.

A conventional general endoscope is configured in such a manner that an insertion unit inserted into the body cavity and an operation unit for controlling the insertion unit are integrally formed with each other, and a plurality of conduits and guides are installed in the insertion unit and the operation unit in such a manner as to internally pass through each unit, particularly an image pickup device such as an expensive CCD is provided at a front end of the insertion unit. However, such a conventional endoscope entails a problem in that it is difficult to separate only the insertion unit from the operation unit to replace it with a new one.

Patent Document 1: KR10-0673412 B1
Patent Document 2: KR10-1091999 B1
Patent Document 3: KR10-1783225 B1

Patent documents 1 to 3 disclose various types of detachable endoscopes that can couple an insertion unit inserted into a body cavity and an operation unit that operates the insertion unit to each other in use, or decouple the insertion unit and the operation unit from each other for storage so as to keep up with a recent trend toward more enhanced hygienic function of the endoscopes used for medical purposes.

However, the detachable endoscopes disclosed in the above Patent Documents have a structure in which the operation unit and the insertion unit are detachably coupled to each other by means of a connection unit. Nevertheless, operating wires for vertically and horizontally operating a front end of the insertion unit inserted into the body cavity perform an incorrect quantitative linear motion and are operated unstably, which contributes to a deterioration of reliability.

SUMMARY OF THE INVENTION

The present invention has been made to solve the above-mentioned problems associated with the prior art, and it is an object of the present invention to provide a detachable endoscope which can stably and precisely perform the quantitative motion of an operating wire of vertically and horizontally bending a front end of an insertion unit inserted into a body cavity while detachably coupling the insertion unit inserted into a body cavity and an operation unit having an operation function to each other.

The technical problems to be solved in the present invention are not limited to the above-mentioned technical problems, and the other technical problems that are not mentioned in the present invention will be apparently understood by one of ordinary skill in the art in the technical field to which the present invention pertains from the following description.

To achieve the above objects, in a preferred embodiment, the present invention provides a detachable endoscope which includes an insertion unit including an illuminating and image pickup unit, an operation unit configured to bendingly operate a front end of the insertion unit, and a detachable unit disposed between the insertion unit and the operation unit and configured to detachably couple the insertion unit and the operation unit to each other, wherein the detachable unit includes: a first detachable module disposed at the insertion unit in such a manner as to connected to respective one ends of first and second operating wire and third and fourth operating wires juxtaposedly arranged in the insertion unit; and a second detachable module disposed at the operation unit in such a manner as to be connected to respective both ends of upper and lower chains wound around upper and lower sprockets of the operation unit, wherein the first detachable module includes: a first module main body disposed within a rear end of the insertion unit and having first, second, third and fourth rectilinear guide through-bores penetratingly formed longitudinally therein, and a central opening penetratingly formed at a center of the main body in a thickness direction of the main body in such a manner as to fluidically communicate with the first, second, third and fourth guide through-bores; first, second, third and fourth rack gears slidably assembled in the first, second, third and fourth rectilinear guide through-bores in such a manner as to be correspondingly coupled at one ends thereof to respective one ends of first, second, third and fourth operating wires; a first pinion gear meshingly disposed between the first and second rack gears; a second pinion gear meshingly disposed between the third and fourth rack gears; and a gear shaft fixedly mounted in the central opening in such a manner that the first and second pinion gears are assembled rotatably so as to be vertically spaced apart from each other by a predetermined interval.

In the detachable endoscope of the present invention, the first, second, third and fourth rack gears may include: one or more rectilinear bars each having a predetermined length, which are respectively slidably assembled in the first, second, third and fourth rectilinear guide through-bores: and one or more rectilinear gear tooth parts each having a predetermined length, which are respectively protrudingly formed on the outer surfaces of the rectilinear bars so as to mesh with gear teeth formed on the outer circumferential surfaces of the first and second pinion gears.

In the detachable endoscope of the present invention, each of the bars of the first, second, third and fourth rack gears may include a movable member disposed thereon so as to guidingly move along each of a plurality of rectilinear guide slits longitudinally formed to be incised on the outer surfaces of both sides of each of the top and bottom portions of the first module main body.

In the detachable endoscope of the present invention, the gear shaft may include first and second annular grooves formed on an outer circumferential surface thereof, which corresponds to the first and second pinion gears, and first and second elastic rings respectively fitted into the first and second annular grooves in such a manner that the outer circumferential surfaces of the first and second elastic rings elastically abut against the inner circumferential surfaces of the first and second pinion gears.

In the detachable endoscope of the present invention, the first detachable module may include: a wire support part configured to support the linear movement of the first, second, third and fourth operating wires, wherein the wire support part may include: first, second, third and fourth support members respectively having support through-holes penetratingly formed therein to allow the first, second, third and fourth operating wires to be correspondingly inserted into the support members therethrough; a support block configured to allow the first, second, third and fourth support members to be fixedly mounted to one end thereof; and a connecting bracket configured to allow the support block 195 to be detachably assembled to one end of the first module main body 180 by means of a plurality of fastening members.

In the detachable endoscope of the present invention, the first, second, third and fourth rack gears may respectively include first, second, third and fourth connecting element respectively disposed at one ends thereof, which correspond to the first, second, third and fourth operating wires, so as to be connected to one ends of the first, second, third and fourth operating wires.

In the detachable endoscope of the present invention, the first, second, third and fourth rack gears may respectively include first, second, third and fourth coupling members respectively disposed at the other ends thereof, which correspond to the second detachable module 200, so as to be hookingly connected to first, second, third and fourth coupled members disposed at one ends of first, second, third and fourth connecting shafts provided at the second detachable module 200.

Effects of the Invention

The detachable endoscope according to a preferred embodiment of the present invention as constructed above has the following effects.

When the insertion unit inserted into the body cavity is contaminated or malfunctions, it can be separated from the operation unit so as to be easily replaced with new one, thereby improving safety, and the contaminated insertion unit can be scrapped and disposed of and a new clean insertion unit is replaceably mounted on the detachable endoscope so that endoscopic surgery can be safely carried out.

The vertical and horizontal bending operation of the front end of the insertion unit can be quantitatively performed in a precise and smooth manner by virtue of the meshing action between the rack gears and the pinion gears, thereby improving convenience in use.

BRIEF DESCRIPTION OF THE DRAWINGS

The above and other objects, features and advantages of the present invention will be apparent from the following detailed description of the preferred embodiments of the invention in conjunction with the accompanying drawings, in which.

DESCRIPTION OF THE PREFERRED EMBODIMENTS

Hereinafter, embodiments of the present invention that can be easily implemented by those skilled in the art to which the present invention pertains will be described in detail with reference to the attached drawings. Further, if, in the description of the principles of the operation of preferred embodiments, detailed descriptions of well-known functions or configurations may unnecessarily make the gist of the present invention obscure, the detailed descriptions thereof will be omitted.

The same reference numerals are used throughout the different drawings to designate components performing the same or similar functions and operations.

Throughout the entire specification, a representation indicating that a first part is "connected" to a second part includes the case where the first part is "indirectly connected" to the second part with some other element interposed therebetween, as well as the case where the first part is "directly connected" to the second part. Further, a representation indicting that a certain part "includes" a certain element means that other elements may be further included in the certain part without excluding other elements unless a description to the contrary is specifically pointed out.

Figure 1:
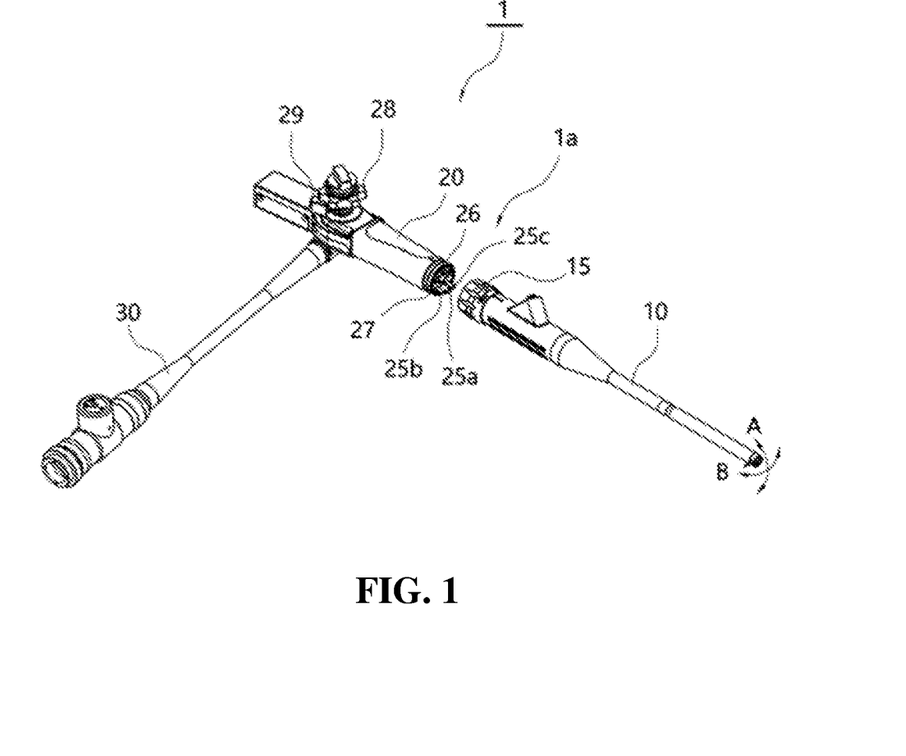
FIG. 1 is a schematic perspective view illustrating a detachable endoscope according to an embodiment of the present invention.

As shown in FIG. 1, a detachable endoscope 1 according to an embodiment of the present invention includes an insertion unit 10 that is inserted at a front end thereof into a body cavity when endoscopic surgery is performed, an operation unit 20 that includes a plurality of operation knobs, a universal joint 30 that is electrically connected to an endoscope control management system, and a detachable unit 1*a* that couples the insertion unit 10 and the operation unit 20 to each other before endoscopic surgery to mechanically interconnect them or mechanically decouples the insertion 10 and the operation unit 20 from each other after endoscopic surgery. The detachable unit 1*a* may be a connector that is configured to detachably connect the insertion unit 10 to the operation unit 20.

The insertion unit 10 is formed of a flexible tubular material so as to adjust a direction where it is inserted into a body cavity. The insertion unit 10 includes an illuminating and image pickup unit having a light source for illuminating the inside of the body cavity and an image sensor for capturing images of the body cavity at a front end thereof.

The operation unit 20 includes an upper operation knob 28 that bendingly operates the front end of the insertion unit inserted into the body cavity in a vertical direction, and a lower operation knob 29 that bendingly operates the front end of the insertion unit in a horizontal direction.

The operation unit 20 internally includes upper and lower sprockets provided at the upper and lower operation knobs, respectively, and upper and lower chains connected to the upper and lower sprockets so that a selective rotational motion of the upper and lower operation knobs is converted into a linear motion, and the upper and lower chains are connected to an inner side of a front end of the insertion unit by means of a plurality of operating wires disposed at the inside of the insertion unit.

Some of the plurality of operating wires disposed within the insertion unit is converted into a linear motion through the upper and lower sprockets rotated by the selective rotation of the upper and lower operation knobs by a user and the upper and lower chains performing a reciprocating rectilinear motion, so the front end of the insertion unit is bendingly operated in a vertical or horizontal direction in a body cavity in response to the linear motion of the operating wires.

The operation unit 20 includes an operation switch and an operation button for charging or discharging liquid or gas for washing and disinfection. In addition, the insertion unit 10 includes an inlet and outlet port formed at a rear end thereof to allow a surgical instrument such as an endoscopic treatment instrument having a clip to advance to or retract from the inlet and outlet port, and a cap configured to open or close the inlet and outlet port, and the rear end of the insertion 10 is detachably coupled to a front of the operation unit 20 by means of the detachable unit.

Figure 2:
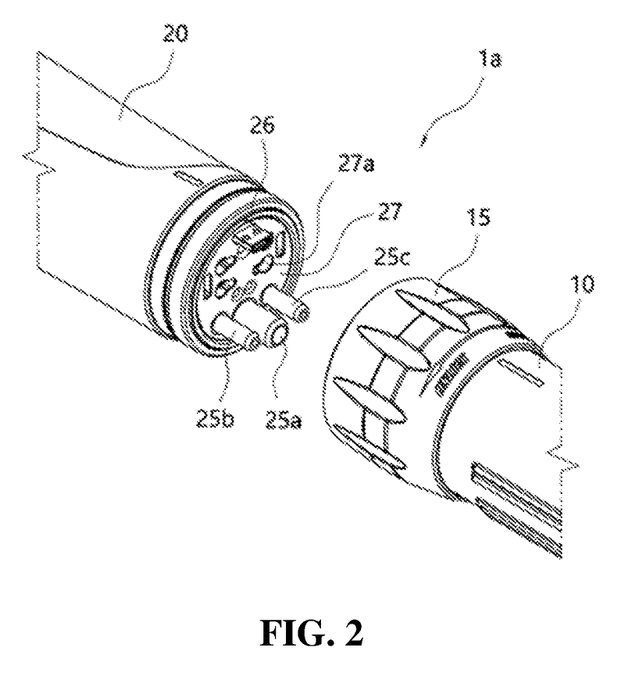
FIG. 2 is an exploded view illustrating a coupling part between a insertion unit and an operation unit of a detachable endoscope according to an embodiment of the present invention.

As shown in FIGS. 1 and 2, an end cover 27 provided at the front end of the operation unit includes an air supply channel 25*b* that supplies air, a water supply channel 25*c* that supplies water, and a suction channel 25*a* that sucks in water and air so as to be discharged to the outside. In addition, the end cover 27 includes a terminal 26 that is electrically connected to the illuminating and image pickup unit of the insertion unit 10. The insertion unit 10 is formed as a generally cylindrical housing and includes a ring-shaped coupling element 15 disposed at the rear end thereof so as to be screw-engaged with a female screw thread formed at the front end of the operation unit 20 formed as a cylindrical housing.

Figure 3:
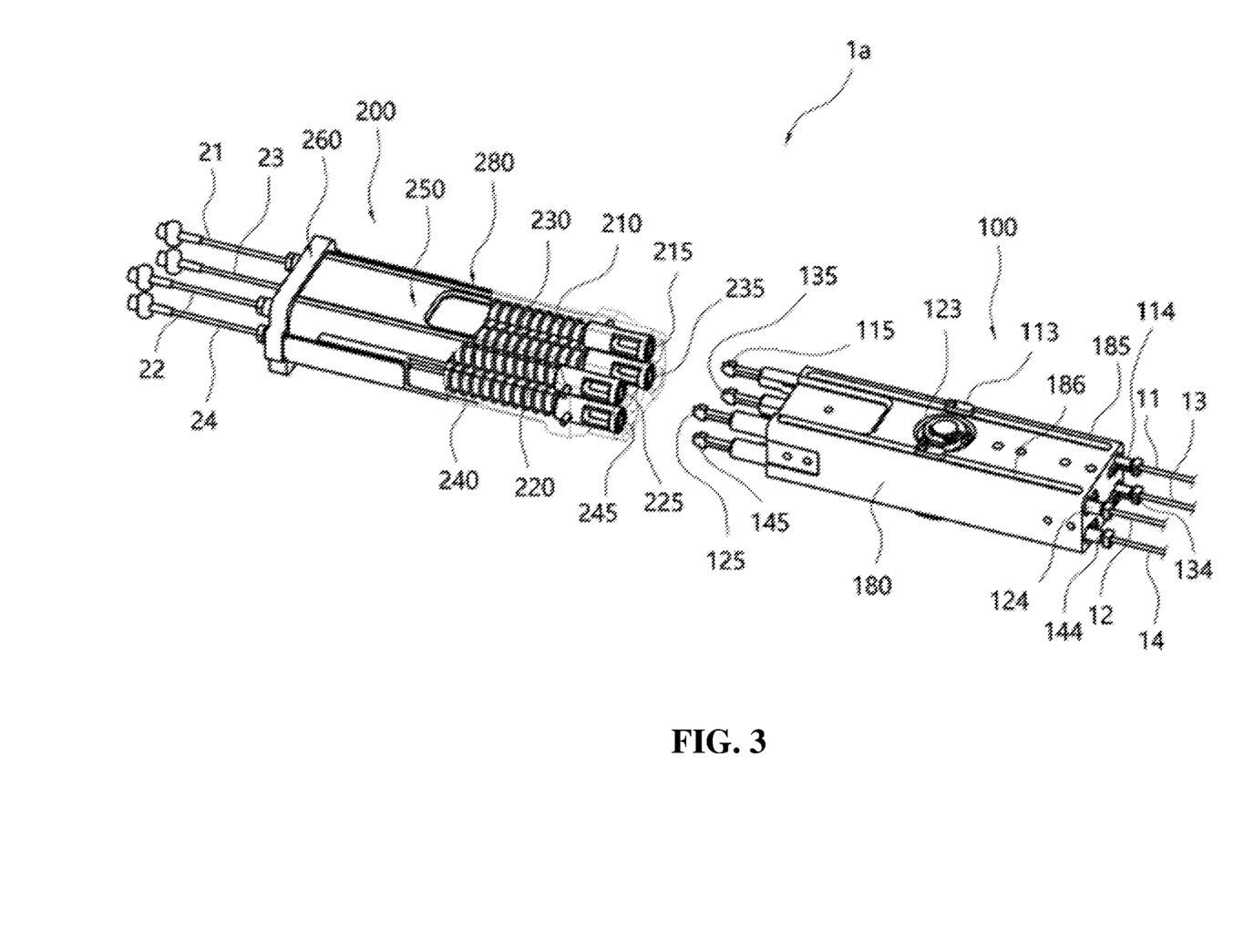
FIG. 3 is an exploded perspective view illustrating a detachable unit of a detachable endoscope according to an embodiment of the present invention.

As shown in FIGS. 2 and 3, the detachable endoscope 1 according to an embodiment of the present invention includes a detachable unit 1*a* that is configured to detachably couple the rear end of the insertion unit and the front end of the operation unit to each other.

The detachable unit 1*a* includes a first detachable module 100 insertedly disposed in the insertion unit 10 and a second detachable module 200 insertedly disposed in the operation unit 20 so as to be correspondingly coupled to the first detachable module 100.

The first detachable module 100 is connected to one ends of first and second operating wires 11 and 12 that are juxtaposedly arranged in the insertion unit to bendingly operate the front end of the insertion unit in a vertical direction (A) and is connected to one ends of third and fourth operating wires 13 and 14 that are juxtaposedly arranged in the insertion unit to bendingly operate the front end of the insertion unit in a horizontal direction (B).

The second detachable module 200 is connected to respective both ends of the upper and lower chains wound around the upper and lower sprockets that are rotated in forward and reverse directions in response to a rotational operation of the upper and lower operation knob 28 and 29 by means of first, second, third and fourth connecting wires 21, 22, 23 and 24.

Herein, although it has been illustrated and described that the first and second connection wires 21 and 22 connected to both ends of the upper chain wound around the upper sprocket bendingly operates the front end of the insertion unit in a vertical direction in cooperation with the first and second operating wires 11 and 12 juxtaposedly arranged in pair at an inner upper side of the insertion unit on the drawing sheet, and that the third and fourth connection wires 23 and 24 connected to both ends of the lower chain wound around the lower sprocket bendingly operates the front end of the insertion unit in a horizontal direction in cooperation with the third and fourth operating wires 13 and 14 juxtaposedly arranged in pair at an inner lower side of the insertion unit on the drawing sheet, the present invention is not limited thereto and the vertical and horizontal bending operations of the front end of insertion unit may be performed in a vice-versa manner depending on design specifications of an endoscope.

In addition, although it has been illustrated and described that the rotation of the upper and lower sprockets is performed by virtue of a manual rotational operation of a worker who grasps the upper and lower operation knobs provided at the operation unit, the present invention is not limited thereto and the rotation of the upper and lower sprockets may be performed in such a manner that a rotary shaft assembled with the upper and lower sprockets is connected to a drive means such as a motor and the drive means is controlled by a separate remote operation means such as a joystick.

As shown in FIGS. 3, 4, 5, 6 and 7, the first detachable module 100 includes first and second rack gears 110 and 120 disposed at an upper side thereof, third and fourth rack gears 130 and 140 disposed at a lower side thereof, a first pinion gear 150 meshingly disposed between the first and second rack gears, a second pinion gear 160 meshingly disposed between the third and fourth rack gears; a gear shaft 170 that couples the first and second pinion gears to each other, and a first module main body 180 that internally accommodates the above-mentioned elements.

The first module main body 180 is a generally rectangular parallelepiped-shaped block structure in which it has first, second, third and fourth rectilinear guide through-bores 181, 182, 183 and 184 penetratingly formed longitudinally therein, and a central opening 189 penetratingly formed at a center of the main body in a thickness direction substantially orthogonal to a longitudinal direction of the main body in such a manner as to fluidically communicate with the first, second, third and fourth guide through-bores 181, 182, 183 and 184.

Respective both ends of the first, second, third and fourth rectilinear guide through-bores 181, 182, 183 and 184 are opened so as to be externally exposed on both end surfaces of the first module main body 180, and both ends of the central opening 189 are opened so as to be externally exposed on the top and bottom surfaces of the first module main body 180.

The first and second rack gears 110 and 120 are rectilinear bar-shaped gear members that are connected at one ends thereof to the first and second operating wires 11 and 12 juxtaposedly arranged at the inner upper side of the insertion unit, and are detachably connected at the other ends thereof to the second detachable module 200. The third and fourth rack gears 130 and 140 are rectilinear bar-shaped gear members that are connected at one ends thereof to the third and fourth operating wires 13 and 14 juxtaposedly arranged at the inner lower side of the insertion unit, and detachably connected at the other ends thereof to the second detachable module.

The first pinion gear 150 is a gear member that is meshingly interposed between the first rack gear 110 and the second rack gear 120 which are juxtaposedly arranged so as to linearly move the first and second rack gears in the opposite directions to each other to bendingly operate the front end of the insertion in the vertical direction upon the rotational operation of the upper operation knob.

The second pinion gear 160 is a gear member that is meshingly interposed between the third rack gear 130 and the fourth rack gear 140 which are juxtaposedly arranged rightly below the first and second rack gears so as to linearly move the third and fourth rack gears in the opposite directions to each other to bendingly operate the front end of the insertion in the horizontal direction upon the rotational operation of the lower operation knob.

The first, second, third and fourth rack gears 110, 120, 130 and 140 respectively include a plurality of rectilinear bars 111, 121, 131 and 141 each having a predetermined length, which are respectively slidably assembled in the first, second, third and fourth rectilinear guide through-bores 181, 182, 183 and 184 and externally exposed at both ends thereof to both side of the first module main body 180, and a plurality of rectilinear gear tooth parts 112, 122, 132 and 142 each having a predetermined length, which are respectively protrudingly formed on the outer surfaces of the rectilinear bars so as to mesh with gear teeth formed on the outer circumferential surfaces of the first and second pinion gears 150 and 160.

Although it has been illustrated and described that the rectilinear gear tooth parts 112, 122, 132 and 142 are respectively formed integrally on the outer surfaces of the rectilinear bars of the first and second rack gears, which confront the first pinion gear, and the outer surfaces of the rectilinear bars of the third and fourth rack gears, which confront the second pinion gear, the present invention is not limited thereto and the rectilinear gear tooth parts 112, 122, 132 and 142 may be formed in a prefabricated manner.

The rectilinear gear tooth parts 112, 122, 132 and 142 are respectively exposed to the outside through communicating slits 112a, 122a, 132a and 142a longitudinally formed to be incised on the inner side of the first module main body 180 to allow the first, second, third and fourth rectilinear guide through-bores and the central opening to communicate with each other therethrough so that the first and second rack gears and the first pinion gear mesh with each other, and the third and fourth rack gears and the second pinion gear mesh with each other.

The first, second, third and fourth rectilinear guide through-bores 181, 182, 183 and 184 may include generally circular cross-sectional guide through-bores 181a, 182a, 183a and 184a whose inner circumferential surfaces guidingly abut against the outer circumferential surfaces of the respective rectilinear bars of the first, second, third and fourth rack gears 110, 120, 130 and 140, extension through-bores 181b, 182b, 183b and 184b formed extending outwardly from the guide through-bores, respectively, to allow the respective gear tooth parts of the first, second, third and fourth rack gears 110, 120, 130 and 140 to be slidably guided therealong without any interferences.

In this case, although it has been illustrated and described that the outer circumferential surfaces of the respective rectilinear bars of the first, second, third and fourth rack gears 110, 120, 130 and 140 and the inner circumferential surfaces of the respective circular cross-sectional guide through-bores of the first, second, third and fourth rectilinear guide through-bores are entirely brought into close contact with each other, the present invention is not limited thereto and the outer circumferential surfaces of the respective rectilinear bars of the first, second, third and fourth rack gears 110, 120, 130 and 140 and the inner circumferential surfaces of the respective circular cross-sectional guide through-bores of the first, second, third and fourth rectilinear guide through-bores partially brought into close contact with each other to reduce the contact area between the outer circumferential surfaces of the respective rectilinear bars and the inner circumferential surfaces of the respective circular cross-sectional guide through-bores, and thus rectilinear protrusions of a predetermined length may be formed in a guide direction on the outer circumferential surfaces of the respective rectilinear bars or the inner circumferential surfaces of the respective circular cross-sectional guide through-bores so that the respective rectilinear bars can perform a rectilinear guide motion smoothly along the inner circumferential surfaces of the respective circular cross-sectional guide through-bores.

A plurality of rectilinear guide slits 185, 186, 187 and 188 are longitudinally formed to be incised on the outer surfaces of both sides of each of the top and bottom portions of the first module main body 180, and the respective rectilinear bars 111, 121, 131 and 141 of the first, second, third and fourth rack gears 110, 120, 130 and 140 includes movable members 113, 123, 133 and 143 disposed thereon so as to guidingly move along the rectilinear guide slits 185, 186, 187 and 188.

The movable members 113, 123, 133 and 143 are detachably assembled in assembly recesses formed depressedly at the lengthwise centers of the top surfaces of the rectilinear bars 111, 121, 131 and 141, and the rectilinear gear tooth parts and the movable members are preferably oriented on the outer surfaces of the rectilinear bars in a crossing arrangement with a phase difference of approximately 90 degrees.

In addition, the first, second, third and fourth rack gears 110, 120, 130 and 140 include first, second, third and fourth connecting elements 114, 124, 134 and 144 disposed at one ends thereof, which correspond to the first, second, third and fourth operating wires 11, 12, 13 and 14, so as to be connected to one ends of the first, second, third and fourth operating wires 11, 12, 13 and 14.

The first, second, third and fourth rack gears 110, 120, 130 and 140 include first, second, third and fourth coupling members 115, 125, 135 and 145 disposed at the other ends thereof, which correspond to the second detachable module 200, so as to be hookingly connected to first, second, third and fourth coupled members 215, 225, 235 and 245 disposed at one ends of first, second, third and fourth connecting shafts 210, 220, 230 and 240 provided at the second detachable module 200.

Herein, it is possible to transfer a power required to selectively reciprocate the first, second, third and fourth operating wires so as to bendingly operate the front end of the insertion unit in the vertical and horizontal directions upon the rotational operation of the upper and lower operation knobs provided at the operation unit by virtue of the hooking connection between the first, second, third and fourth coupling members 115, 125, 135 and 145 of the first, second, third and fourth rack gears 110, 120, 130 and 140, and the first, second, third and fourth coupled members 215, 225, 235 and 245 of the first, second, third and fourth connecting shafts 210, 220, 230 and 240.

The gear shaft 170 is an axial member that is inserted into and fixedly mounted in the central opening 189 of the first module main body in such a manner that the first and second pinion gears 150 and 160 meshing with the first, second, third and fourth rack gears 110, 120, 130 and 140 are assembled rotatably so as to be vertically spaced apart from each other by a predetermined interval.

The gear shaft 170 includes a plate bracket 173 integrally assembled by a fastening member at a lower end thereof in such a manner as to cover one opened end of the central opening 189 and abut against the outer bottom surface of the first module main body, and an escape-preventing clip 156 disposed at an upper end thereof so as to prevent the first and second pinion gears from escaping to the outside.

A first cylindrical sleeve 155 is interposed between the first pinion gear 150 and the escape-preventing clip 156 to maintain a gap therebetween, and a second cylindrical sleeve 165 is interposed between the first pinion gear 150 and the second pinion gear 160 to maintain a gap therebetween.

The gear shaft 170 includes first and second annular grooves formed on an outer circumferential surface thereof, which corresponds to the first and second pinion gears 150 and 160, and first and second elastic rings 171 and 172 made of a rubber material, which are respectively fitted into the first and second annular grooves in such a manner that the outer circumferential surfaces of the first and second elastic rings elastically abut against the inner circumferential surfaces of the first and second pinion gears 150 and 160.

By virtue of the elastic contact between the inner circumferential surfaces of the first and second pinion gears 150 and 160 and the outer circumferential surfaces of the first and second elastic rings 171 and 172, a noise caused by a backlash occurring during the meshing action between the first and second rack gears 110 and 120 and the first pinion gear 150 and between the third and fourth rack gears 130 and 140 and the second pinion gear 160 can be reduced, and the first and second rack gears can be linearly moved more smoothly in the opposite direction to each other without having to use a lubricant and the third and fourth rack gears can also be linearly moved more smoothly in the opposite direction to each other without having to use a lubricant during the vertical and horizontal bending operation of the front end of the insertion unit.

Figure 4:
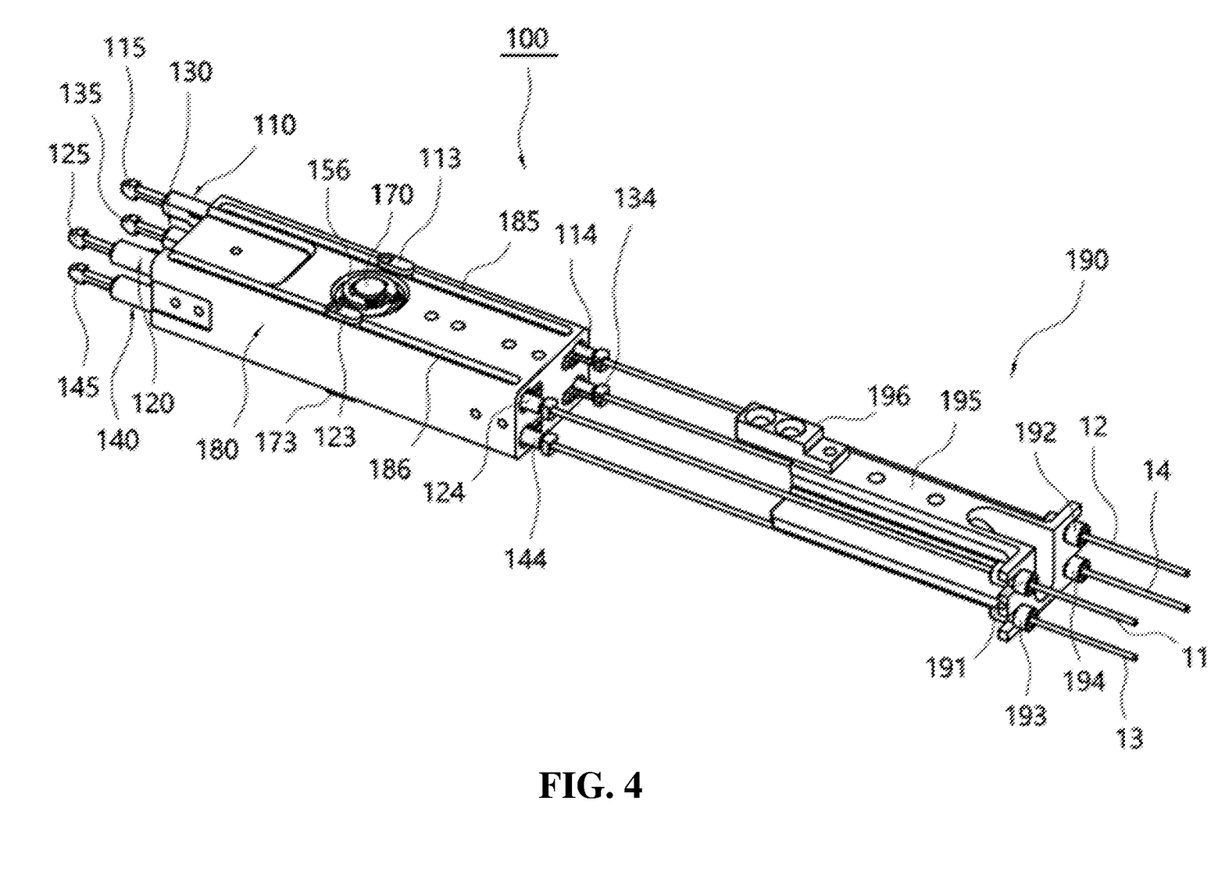
FIG. 4 is an perspective view illustrating a first detachable module of a detachable unit of a detachable endoscope according to an embodiment of the present invention.
Figure 5:
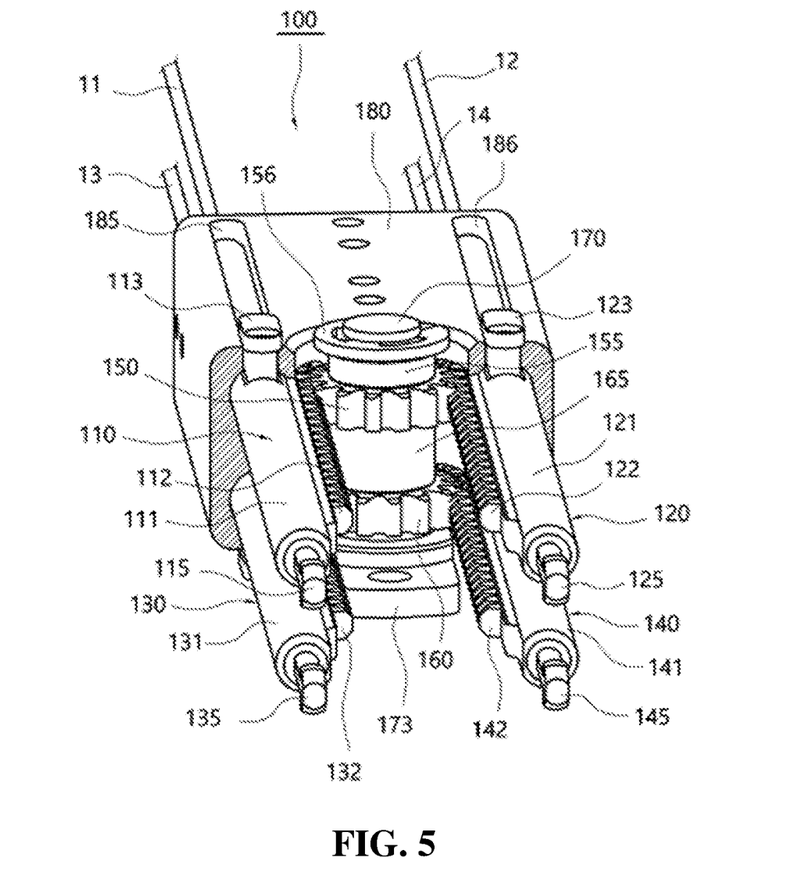
FIG. 5 is a cross-sectional perspective view illustrating a first detachable module of a detachable unit of a detachable endoscope according to an embodiment of the present invention.
Figure 6:
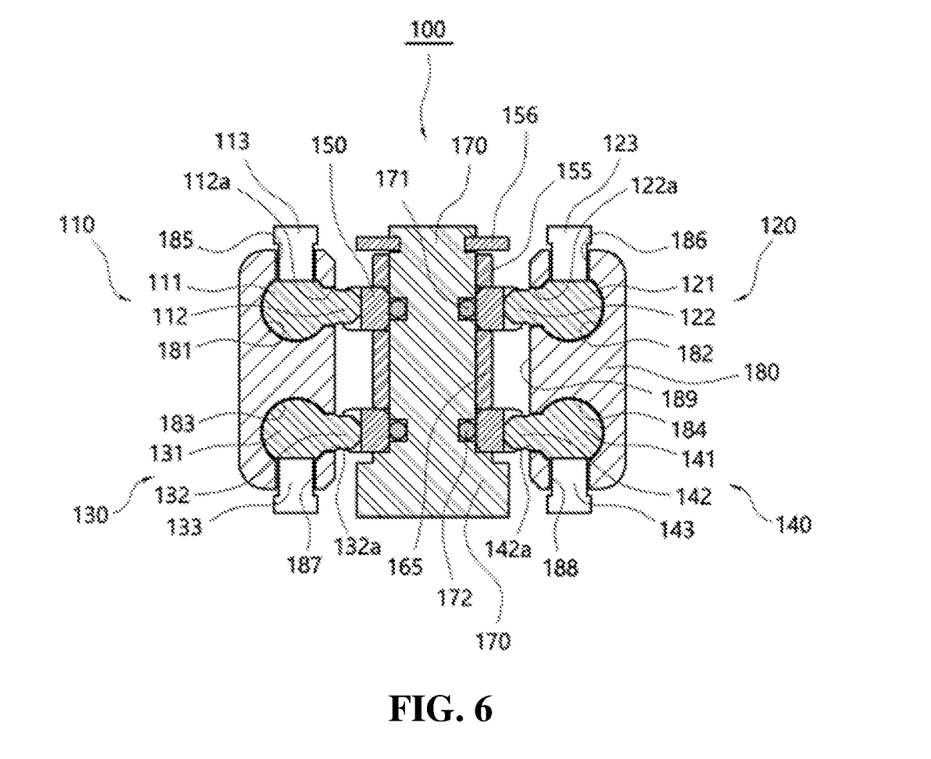
FIG. 6 is a vertical transverse cross-sectional view illustrating a first detachable module of a detachable unit of a detachable endoscope according to an embodiment of the present invention.
Figure 7:
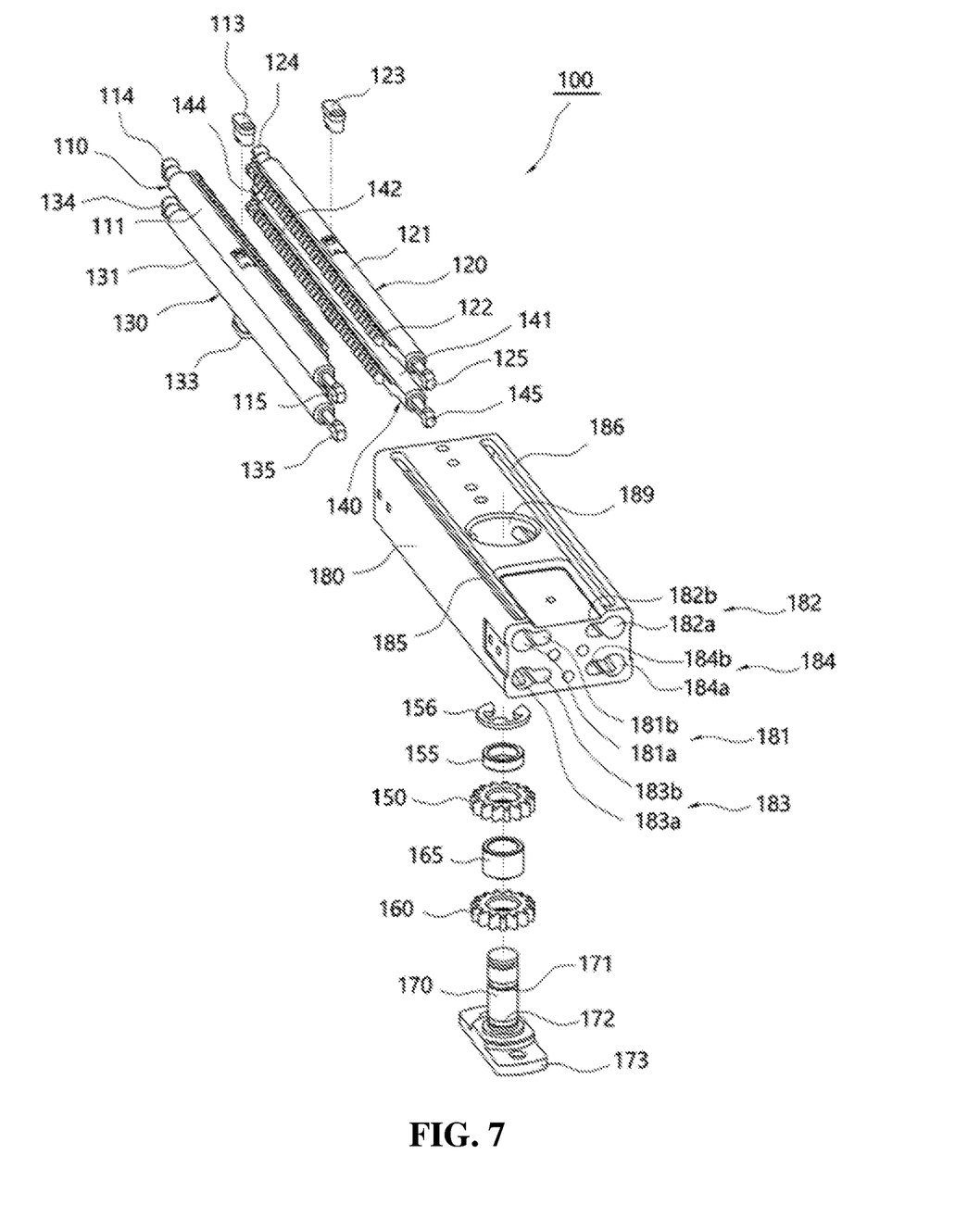
FIG. 7 is an exploded perspective view illustrating a first detachable module of a detachable unit of a detachable endoscope according to an embodiment of the present invention.

Further, as shown in FIG. 4, the first detachable module 100 may include a wire support part 190 that supports the linear movement of the first, second, third and fourth operating wires 11, 12, 13 and 14 connected to one ends of the first, second, third and fourth rack gears.

The wire support part 190 includes: first, second, third and fourth support members 191, 192, 193 and 194 having support through-holes penetratingly formed therein to allow the first, second, third and fourth operating wires 11, 12, 13 and 14 to be correspondingly inserted into the support members therethrough; a support block 195 configured to allow the first, second, third and fourth support members to be fixedly mounted to one end thereof; and a connecting bracket 196 configured to allow the support block 195 to be detachably assembled to one end of the first module main body 180 by means of a plurality of fastening members.

Each of the first, second, third and fourth support members 191, 192, 193 and 194 is formed as a cylindrical member having a support through-hole penetratingly formed at the center of a body thereof and an annular groove formed on the outer circumferential surface thereof, and the support block 195 includes a plurality of fitting fixed pieces formed at the one end thereof so as to be correspondingly fixedly fitted into the annular grooves formed on the outer circumferential surfaces of the first, second, third and fourth support members.

Figure 8A:
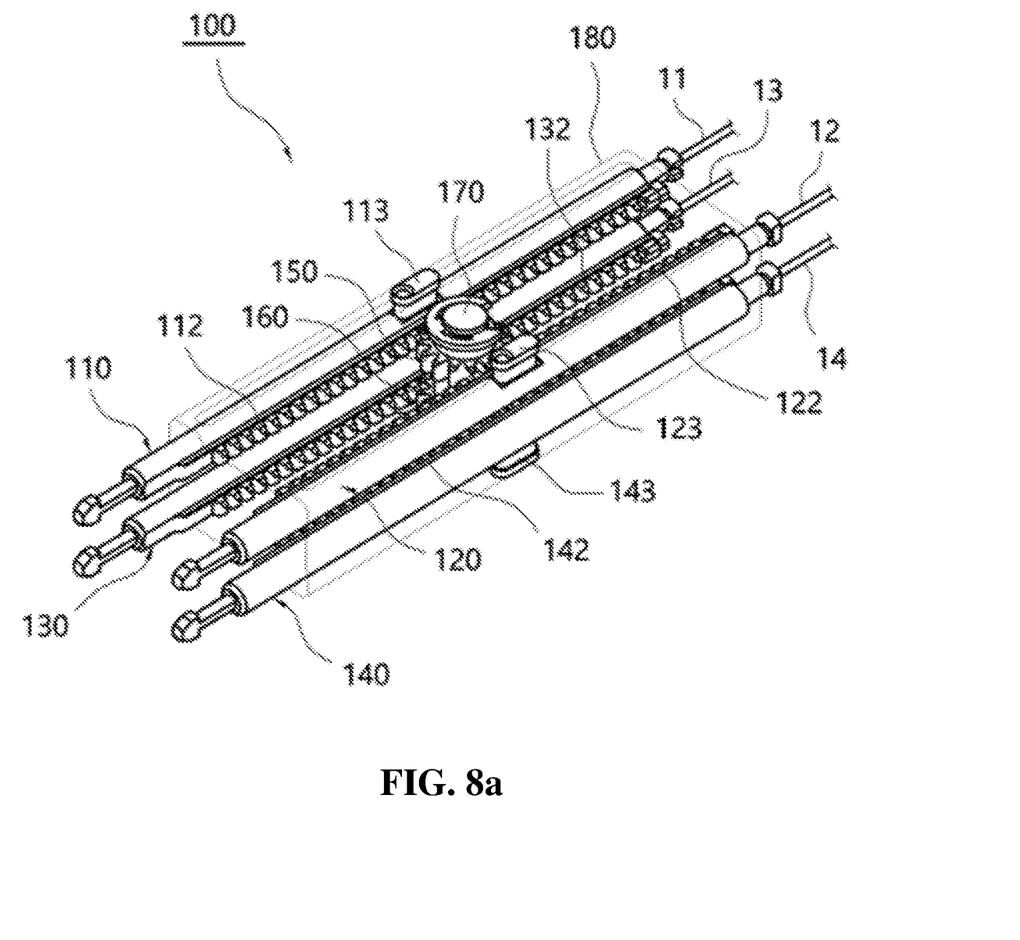
FIGS. 8*a*, 8*b* and 8*c* illustrate the operating state of a first detachable module of a detachable unit of a detachable endoscope according to an embodiment of the present invention.

In the first detachable module 100 as constructed above, the respective front ends of the first, second, third and fourth coupling members corresponding to the second detachable module of the operation unit are positioned on the same vertical plane in an initial standby state in which the first and second pinion gears 150 and 160 are positioned at the lengthwise center of the first, second, third and fourth rack gears 110, 120, 130 and 140 as shown in FIG. 8a.

In this state, when the first detachable module and the second detachable module are correspondingly connected to each other while the rear end of the insertion unit and the front end of the operation unit are correspondingly coupled to each other, the first, second, third and fourth coupling members 115, 125, 135 and 145 disposed at the first, second, third and fourth rack gears 110, 120, 130 and 140 of the first detachable module 100 can be hookingly connected to the first, second, third and fourth coupled members 215, 225, 235 and 245 of the first, second, third and fourth connecting shafts 210, 220, 230 and 240 of the second detachable module 200.

Figure 8B:
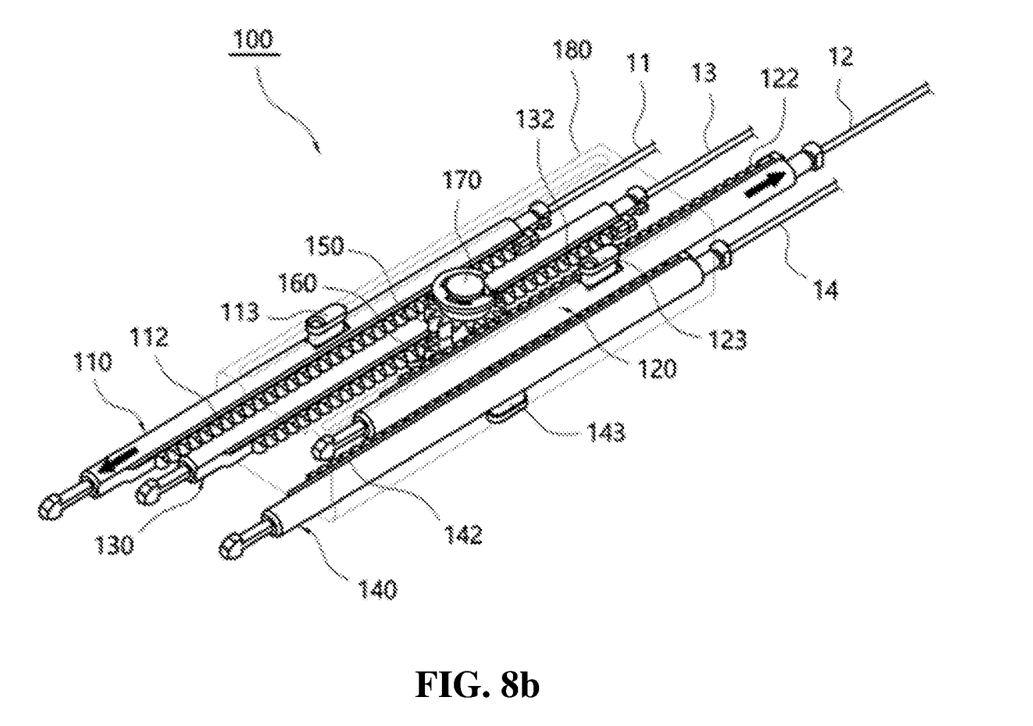

In addition, in the state in which the first, second, third and fourth coupling members 115, 125, 135 and 145, and the first, second, third and fourth coupled members 215, 225, 235 and 245 are hookingly connected to each other, when the first rack gear moves leftwards by a predetermined distance on the drawing sheet as shown in FIG. 8b by a forward rotation of the upper operation knob 28 provided at the operation unit, the second rack gear linearly moves rightwards, i.e., in the reverse direction to the moving direction of the first rack gear by the same predetermined distance as the moving distance of the first rack gear by virtue of the meshing action between the first and second rack gears and the first pinion gear to cause the first operating wire to be pullingly moved quantitatively and simultaneously the second operating wire to be pushingly moved quantitatively, so that the front end of the insertion unit can be bendingly operated upwards a given angle in proportional to the amount of the forward rotation of the upper operation knob 28.

Figure 8C:
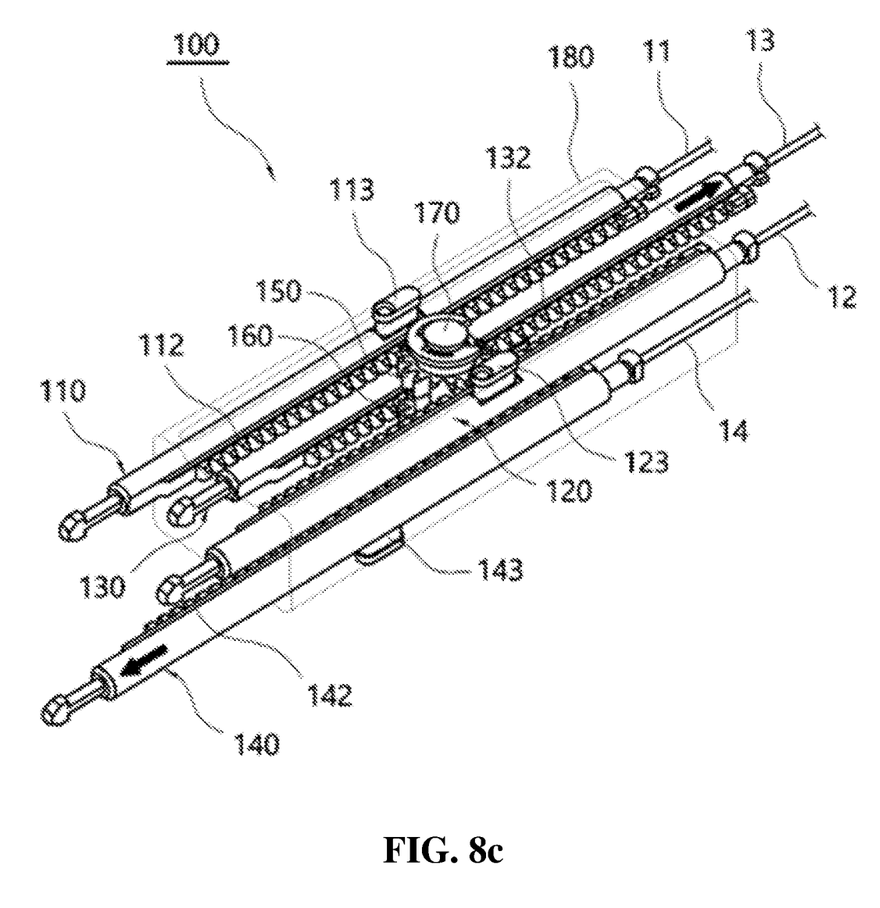

On the contrary, when the second rack gear moves leftwards by a predetermined distance on the drawing sheet as shown in FIG. 8c by a reverse rotation of the upper operation knob 28, the first rack gear linearly moves rightwards, i.e., in the reverse direction to the moving direction of the second rack gear by the same predetermined distance as the moving distance of the second rack gear by virtue of the meshing action between the first and second rack gears and the first pinion gear to cause the second operating wire to be pullingly moved quantitatively and simultaneously the first operating wire to be pushingly moved quantitatively, so that the front end of the insertion unit can be bendingly operated downwards by a given angle in proportional to the amount of the reverse rotation of the upper operation knob 28.

In addition, the third and fourth rack gears linearly move by a predetermined distance in the reverse direction to each other by a forward or reverse rotation of the lower operation knob 29 provided in the operation unit to cause the third and fourth operating wires to be pullingly or pushingly moved in the reverse direction to each other, so that the front end of the insertion unit can be bendingly operated by a given angle in the horizontal direction, but this linear movement of the third and fourth rack gears is the same as the linear movement of the first and second rack gears, and thus a detailed description thereof will be omitted to avoid redundancy.

Accordingly, during endoscopic surgery, the front end of the insertion unit inserted into a body cavity is bendingly operated in the vertical and horizontal directions by a selective rotational operation of the upper and lower operation knobs provided at the operation unit so that a surgeon can illuminate a lesion in the body cavity and capture an image of the lesion to examine the image, and can remove or treat the lesion examined through a treatment instrument advancing to the inside of the insertion unit.

While the present invention has been described in connection with the exemplary embodiments illustrated in the drawings, they are merely illustrative and the invention is not limited to these embodiments and the accompanying drawings. It will be appreciated by a person having an ordinary skill in the art that various equivalent substitutions, modifications and variations of the embodiments can be made without departing from the spirit and scope of the present invention. Therefore, the true technical scope of the present invention should be defined by the technical spirit of the appended claims.

What is claimed is:

1. A detachable endoscope comprising:
    an insertion unit including an illuminating and image pickup unit;
    an operation unit including at least one operation knob and configured to operate a front end of the insertion unit to be bent; and
    a detachable connector disposed between the insertion unit and the operation unit and configured to detachably couple the insertion unit and the operation unit to each other,
    wherein the detachable connector comprises:
    a first detachable module disposed at the insertion unit to be connected to first, second, third, and fourth operating wires arranged in the insertion unit; and
    a second detachable module disposed at the operation unit to be connected to upper and lower chains wound around upper and lower sprockets of the operation unit,
    wherein the first detachable module comprises:
    a first module main body disposed within the insertion unit and having guide through-bores formed in a longitudinal direction of the main body, and a central opening formed at a center of the main body in a thickness direction of the main body to communicate with the guide through-bores;
    a plurality of rack gears slidably assembled in the guide through-bores to be correspondingly coupled to the first, second, third, and fourth operating wires;
    a first pinion gear disposed between first and second rack gears of the plurality of rack gears;
    a second pinion gear disposed between third and fourth rack gears of the plurality of rack gears; and
    a gear shaft fixedly mounted in the central opening such that the first and second pinion gears are rotatably assembled to the gear shaft to be vertically spaced apart from each other by a predetermined interval.

2. The detachable endoscope according to claim 1, wherein each of the first, second, third and fourth rack gears comprises:
    a rectilinear bar slidably assembled in the respective guide through-bore; and
    rectilinear gear teeth formed on an outer surface of the rectilinear bar so as to mesh with gear teeth formed on an outer circumferential surface of one of the first and second pinion gears.

3. The detachable endoscope according to claim 2, wherein the rectilinear bar comprises a movable member disposed thereon and configured to move along a guide slit formed on an outer surface of the first module main body.

4. The detachable endoscope according to claim 1, wherein the gear shaft comprises:
    first and second annular grooves formed on an outer circumferential surface thereof to correspond to the first and second pinion gears; and
    first and second elastic rings respectively fitted into the first and second annular grooves in such a manner that outer circumferential surfaces of the first and second elastic rings elastically abut against inner circumferential surfaces of the first and second pinion gears.

5. The detachable endoscope according to claim 1, wherein the first detachable module comprises:
    support members having support through-holes formed therein to allow the operating wires to be inserted into the support members therethrough;
    a support block configured to allow the support members to be mounted thereto; and
    a connecting bracket configured to allow the support block to be detachably assembled to one end of the first module main body by means of a plurality of fastening members.

6. The detachable endoscope according to claim 1, wherein each of the first, second, third and fourth rack gears comprises a connecting element disposed at one end thereof to be connected to the respective operating wire.

7. The detachable endoscope according to claim 6, wherein each of the first, second, third and fourth rack gears comprises a coupling member disposed at another end thereof to be connected to a coupled member disposed at one end of a connecting shaft of the second detachable module.

* * * * *